United States Patent [19]

Rosenthal et al.

[11] 3,935,278

[45] Jan. 27, 1976

[54] PROCESS FOR PREPARING DIPEROXIDE FROM AN ORGANIC HYDRO-PEROXIDE AND A KETONE

[75] Inventors: Rudolph Rosenthal, Broomall, Pa.; Harold A. Sorgenti, Olympia Fields, Ill.

[73] Assignee: Atlantic Richfield Company, Los Angeles, Calif.

[22] Filed: Mar. 4, 1970

[21] Appl. No.: 16,564

[52] U.S. Cl. ............................................ 260/610 R
[51] Int. Cl.² ...................................... C07C 179/02
[58] Field of Search ..................... 260/610 R, 610 A

[56] References Cited
UNITED STATES PATENTS

| | | | |
|---|---|---|---|
| 2,455,569 | 12/1948 | Dickey | 260/610 R |
| 2,537,853 | 1/1951 | Pezzaglia | 260/610 R |
| 3,434,975 | 3/1969 | Sheng | 260/610 R |

OTHER PUBLICATIONS

Dickey et al., "J. Amer. Chem. Soc." Vol. 71, pp. 1432–1434

*Primary Examiner*—James O. Thomas, Jr.
*Assistant Examiner*—W. B. Lone
*Attorney, Agent, or Firm*—John R. Ewbank

[57] ABSTRACT

Diperoxides, useful as free radical type polymerization initiators, for example, are preparable from an organic hydroperoxide such as t-butyl hydroperoxide, and a ketone using catalyst comprising molybdenum or vanadium.

5 Claims, No Drawings

PROCESS FOR PREPARING DIPEROXIDE FROM AN ORGANIC HYDRO-PEROXIDE AND A KETONE

BACKGROUND OF THE INVENTION

1. Field of the Invention

This invention relates to a novel method for preparing diperoxides from organic hydroperoxides and ketones.

2. Description of the Prior Art

The prior art, for example, Dickey, U.S. Pat. No. 2,455,569 (Dec. 7, 1948) and Dickey et al, J. Am. Chem. Society, 71, 1432 (1949), shows the reaction of tertiary organic hydroperoxides and ketones to take place only in the presence of inorganic acid or acid-acting catalyst, and preferably in the presence of a dehydrating agent, and the reaction product to be the corresponding diperoxides.

Before this invention, molybdenum and vanadium catalysts were known in certain oxidation reactions including epoxidation of olefin reactions. It was never suggested, and thus it was highly unexpected, that molybdenum and vanadium catalysts would be useful in an organic hydroperoxide ketone condensation reaction.

SUMMARY OF THE INVENTION

It has unexpectedly been discovered that organic hydroperoxides and ketones can be reacted to substantial completion to diorganoperoxyalkanes or cycloalkanes in relatively short times at mild conditions in the absence of acids and dehydrating agents in the presence of molybdenum or vanadium catalyst.

DESCRIPTION OF PREFERRED EMBODIMENTS

The invention is directed to a novel process for the preparation of diperoxides of the formula

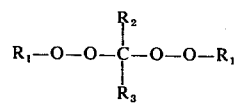

wherein $R_1$, $R_2$ and $R_3$ are independently selected saturated, substituted or unsubstituted organic radicals containing from one to sixteen carbon atoms and wherein $R_2$ and $R_3$ can be joined in an alicyclic radical by the reaction of an organic hydroperoxide of the formula $R_1$—O—O—H and a ketone of the formula

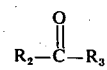

in the presence of molybdenum or vanadium.

The reaction is carried out at temperatures in the range of $-10°C$. to $100°C$., depending on the particular starting materials. Preferred temperatures are 20° to 50°C., and especially preferred is room temperature range of 20° to 30°C.

Atmospheric pressure is preferred for convenience, however, pressures from 0.1 to 100 atmospheres can be used.

Either batch or continuous operation is possible.

The diorganoperoxyalkanes and cycloalkanes produced have utility for various purposes, among which is use as free radical polymerization initiators.

The organic hydroperoxide suitable in this reaction is any of the formula $R_1$—O—O—H wherein $R_1$ is as defined above. Preferably, $R_1$ contains from 4 to 16 carbon atoms. Highly preferred are tertiary alkyl hydroperoxides, and particularly t-butyl hydroperoxide because of its availability in commerce.

Other less preferred organic hydroperoxides suitable are t-amyl, cumene, cyclohexyl, chlorocumene, cymene and so on.

The ketone compound is of the formula

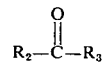

wherein $R_2$ and $R_3$ are as defined as above. Illustrative ketones are acetone, methyl ethyl ketone, methyl n-propyl ketone, methyl isopropyl ketone, diethyl ketone, methyl n-butyl ketone, ethyl n-propyl ketone, methyl isobutyl ketone, ethyl isopropyl ketone, methyl sec. butyl ketone, and the like and their homologues and suitable substitution products such as those in which various substituents are present in lieu of one or more of the hydrogen atoms of the above-defined ketones. For example, hydroxy ketones such as acetyl carbinol, propionyl carbinol, butyryl carbinol, acetoin, diacetone alcohol, acetopropyl alcohol, acetobutyl alcohol, and the like, may be reacted with hydroperoxides of the above class. Also, dicarbonyl compounds of the type of acetyl acetone, as well as the ketone acids, such as pyruvic acid, acetoacetic acid, levulinic acid, mesitonic acid, and the like can be employed. Still another sub-group of the ketone compounds includes the alicyclic ketones, e.g., cyclopentanone, cyclohexanone, as well as derivatives thereof in which one or more of the hydrogen atoms of the nucleus are substituted by alkyl, aryl, alkaryl, aralkyl and/or alicyclic radicals, which radicals are optionally further substituted. Also, included in the class of carbonyl compounds which can thus be reacted with the specified hydroperoxides are the aromatic compounds containing a carbonyl group, e.g., acetophenone and benzophenone.

The catalyst, which constitutes the novelty of the process of this invention, is molybdenum or vanadium, the former being preferred. The metal catalyst is suitably added as a complex with any radical such that it will be soluble in the reaction mixture. Exemplary complexes are the naphthenates, acetates, acetylacetonates, hexacarbonyls, oxides, chlorides, oxychlorides, fluorides, phosphates, sulfides, heteropolyacids and sodium and potassium salts thereof. Mixtures are also suitable.

The molybdenum catalyst can also be added as a complex with an organic hydroperoxide and a lower molecular weight mono or polyhydroxy alcohol, prepared in accordance with the teachings of Sheng et al, U.S. Pat. No. 3,434,975, Mar. 25, 1969.

The amounts of catalyst suitable include from about 0.01 weight percent to about 2 weight percent of metal, based upon total weight of the starting mixture. The most economical operation appears to be achievable at about 0.1 to 0.7 weight percent metal based on total weight of the starting mixture.

The ratios of organic hydroperoxide to ketone in the molar ratio ranges from about 1:100 to 100:1, with preferred ranges being from about 100:4 to 1:10, with maximum yields obtained at around 2:1.

Solvents are not necessary to the reaction, but any solvent which does not react could be employed if desired. An example of a solvent which can be used is t-butanol (especially when t-butyl hydroperoxide is used as the organic hydroperoxide).

The products of the reaction are recovered by known procedures, for example, if the particular ketone is water soluble, the reaction can be diluted with water and the diperoxide separated as the non-aqueous phase. If the starting ketone is insoluble in water, low pressure distillation or extraction with aqueous ethanol are suitable recovery methods.

The following examples are illustrative but are not intended to be limiting.

EXAMPLES 1 to 4

Mixtures with the compositions shown below were made up and allowed to stand at room temperature for the time periods shown. In these experiments the molybdenum catalyst was one prepared by reaction of molybdenum metal with a mixture of t-butyl hydroperoxide and t-butanol in the presence of propylene glycol (U.S. Pat. No. 3,434,975) and contained 5000 ppm Mo.

|  |  | Ex. 1 | Ex. 2 | Ex. 3 | Ex. 4 |
|---|---|---|---|---|---|
| t-butyl hydroperoxide | (g) | 5.3 | 5.3 | 5.3 | 5.3 |
| t-butanol | (g) | 4.4 | 4.4 | 4.4 | 4.5 |
| acetone | (g) | 0.2 | 0.2 | 0.2 | 0.2 |
| formic acid | (g) | 0.1 | 0.1 | 0.1 | 0 |
| Mo catalyst | (g) | 0 | 0.01 | 0.4 | 0.4 |
| Mo | (ppm) | 0 | 5 | 192 | 192 |
| wt. % 2,2-bis(t-butylperoxy)propane |  |  |  |  |  |
| 4 hrs. |  | 0.28 | 0.31 | 1.36 | 1.71 |
| 24 hrs |  | 0.29 | 0.33 | 3.61 | 4.04 |

These experiments show that although only 5 ppm Mo has very little effect on the reaction, the addition of about 200 ppm Mo shows a strong catalytic effect even in the absence of formic acid.

EXAMPLES 5 to 7

To show the effect of higher amounts of Mo catalyst on the reaction, additional runs were made at room temperature. In these runs the catalyst used was a commercial molybdenum naphthenate catalyst containing 5 wt. % Mo.

|  |  | Ex. 5 | Ex. 6 | Ex. 7 |
|---|---|---|---|---|
| t-butyl hydroperoxide | (g) | 5.3 | 5.3 | 5.3 |
| t-butanol | (g) | 4.5 | 4.5 | 4.5 |
| acetone | (g) | 0.2 | 0.2 | 0.2 |
| 5 wt. % Mo catalyst | (g) | 0.12 | 0.20 | 1.0 |
| Mo | (ppm) | 593 | 980 | 4,545 |
| wt. % 2,2-bis(t-butylperoxy)propane |  |  |  |  |
| 1 hr. |  | — | — | 5.8 |
| 4 hr. |  | 2.5 | 6.3 | 5.8 |
| 24 hr. |  | 4.8 | 6.3 | 5.8 |

These results show that reaction rate increases with increasing Mo catalyst concentration. The reaction is essentially complete in about 4 hours at a Mo concentration of about 1,000 ppm and is essentially complete in about one hour at the 4,000–5,000 ppm Mo concentration range.

EXAMPLES 8 and 9

The previous runs were made with low acetone concentrations in mixtures of t-butyl hydroperoxide-t-butanol to simulate products obtainable by liquid phase oxidation of isobutane. To show that the molybdenum catalyst is effective in other mixtures, runs were made using mixtures of only t-butyl hydroperoxide and acetone in 10:1 weight ratio at room temperature. Results are as follows:

|  |  | Ex. 8 | Ex. 9 |
|---|---|---|---|
| t-butyl hydroperoxide | (g) | 25.0 | 25.0 |
| acetone | (g) | 2.5 | 2.5 |
| 5 wt. % Mo catalyst of Example 5–7 | (g) | 0 | 0.5 |
| Mo | (ppm) | 0 | 980 |
| wt. % 2,2-bis(t-butylperoxy)propane |  |  |  |
| 6 hrs. |  | <0.2 | 21.3 |
| 24 hrs. |  | <0.2 | 32.0 |

EXAMPLES 10 to 15

Reaction of t-Butyl Hydroperoxide with Methyl Ethyl Ketone & with Cyclohexanone

|  |  | Ex.10 | Ex.11 | Ex.12 | Ex.13 | Ex.14 | Ex.15 |
|---|---|---|---|---|---|---|---|
| t-butyl hydroperoxide | (g) | 5.3 | 5.3 | 5.3 | 5.3 | 5.3 | 5.3 |
| t-butanol | (g) | 4.5 | 4.5 | 4.5 | 4.5 | 4.5 | 4.5 |
| methyl ethyl ketone | (g) | 0.2 | 0.2 | 0.2 | 0 | 0 | 0 |
| cyclohexanone | (g) | 0 | 0 | 0 | 0.2 | 0.2 | 0.2 |
| 5 wt % Mo catalyst of Example 5-7 | (g) | 0 | 0.12 | 0.20 | 0 | 0.12 | 0.20 |
| Mo | (ppm) | 0 | 593 | 980 | 0 | 593 | 980 |
| wt % 2,2-bis(t-butylperoxy)butane or 1,1-bis(t-butylperoxy)cyclohexane |  |  |  |  |  |  |  |
| 4 hrs. |  | 0 | 1.0 | 1.9 | 0 | 0.1 | 0.8 |
| 24 hrs. |  | 0 | 2.0 | 2.0 | 0 | 0.7 | 1.1 |

These results show that although the reaction rates are somewhat slower with these ketones the catalytic effect of molybdenum is clear.

EXAMPLES 16 to 19

Reaction of t-Butyl Hydroperoxide with Other Ketones Using Higher Ketone Concentrations Although Examples 10 – 15 show that molybdenum catalyzes the condensation of t-butyl hydroperoxide with other ketones, the effect is seen more clearly in the following experiments:

|  |  | Ex. 1 | Ex. 2 | Ex. 3 | Ex. 4 |
|---|---|---|---|---|---|
| t-butyl hydroperoxide | (g) | 5.0 | 5.0 | 5.0 | 5.0 |
| cyclohexanone | (g) | 0.5 | 0.5 | 0 | 0 |
| methyl ethyl ketone | (g) | 0 | 0 | 0.5 | 0.5 |
| 5 wt. % Mo catalyst of Example 5–7 | (g) | 0 | 0.1 | 0 | 0.1 |
| Mo | (ppm) | 0 | 900 | 0 | 900 |
| wt % 2,2-bis(t-butylperoxy)butane or 1,1-bis(t-butylperoxy)cyclohexane | | | | | |
|  | 4 hrs. | 0 | 8.0 | <0.1 | 12.5 |

EXAMPLE 20

Effect of Temperature

Although reaction rate increases with increasing temperature the rate of decomposition also increases. This is shown by a run made at 93°C. At the end of one hour the concentration of 2,2-bis(t-butylperoxy)propane was 1.83 wt. %, but this decreased to 0.74 wt. % at the end of 4 hours. It is therefore preferable to operate at temperatures below about 50°C.

| t-butyl hydroperoxide | (g) | 5.3 |
|---|---|---|
| t-butanol | (g) | 4.4 |
| acetone | (g) | 0.2 |
| formic acid | (g) | 0.1 |
| Mo catalyst (5000 ppm) of Example 1–4 | (g) | 0.4 |
| Mo | (ppm) | 192 |
| wt % 2,2-bis(t-butylperoxy)propane | | |
|  | 1 hr. | 1.83 |
|  | 4 hrs | 0.74 |

EXAMPLE 21

An experiment was run using a 10:1 weight ratio of t-butyl hydroperoxide to acetone with 1,050 ppm of vanadium (added as a commercial 3 wt. % vanadium naphthenate). Results show that vanadium will also catalyze the condensation of t-butyl hydroperoxide and acetone, but the reaction rate is much slower than when a similar amount of molybdenum catalyst is used.

| t-butyl hydroperoxide | (g) | 5.0 |
|---|---|---|
| acetone | (g) | 0.5 |
| 3 wt. % vanadium naphthenate | (g) | 0.2 |
| V | (ppm) | 1,050 |
| wt. % 2,2-bis(t-butylperoxy)propane | | |
|  | 4 hrs. | 2.0 |
|  | 48 hrs. | 4.3 |

EXAMPLE 22 - Comparative

Experiments otherwise identical to those shown in Examples 1 and 21 were carried out using other metals in place of the molybdenum or vanadium as catalysts. These included chromic acetate, zirconium acetylacetonate, manganic acetylacetonate, cobaltic acetylacetonate, ferrous acetylacetonate, thorium naphthenate and tungsten hexacarbonyl. In all cases the concentration of metal was in the 200–1500 ppm range. None of the metals showed a catalytic effect on the formation of the diperoxide.

Although the invention has been described in considerable detail, and several specific embodiments have been presented, many modifications and departures may be made from the exact construction described herein without departing from the spirit and scope of the invention.

We claim:

1. In a method for preparing compounds of the formula

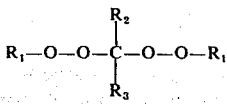

wherein $R_1$, $R_2$ and $R_3$ are independently selected from hydrocarbyl radicals containing from one to sixteen carbon atoms and wherein $R_2$ and $R_3$ can be joined in an alicyclic radical, by the reaction of organic hydroperoxide of the formula $R_1$—O—O—H with a compound of the formula

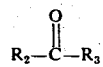

at temperatures in the range of −10°C. to 100°C., the improvement of carrying out the reaction in the presence of a catalyst concentration within the range from about 0.01 to 2 weight percent of metal based upon the total weight of the starting materials, said catalyst being molybdenum or vanadium compounds or complexes soluble in the reaction mixture.

2. The process of claim 1 wherein the reaction is carried out in the presence of both molybdenum and vanadium compounds or complexes.

3. The process of claim 1 wherein said organic hydroperoxide is selected from the group consisting of tertiary amyl hydroperoxide, cumene hydroperoxide, cyclohexyl hydroperoxide, cymene hydroperoxide, and tertiary butyl hydroperoxide, and in which the $R_2$—CO—$R_3$ ketone is selected from the group consisting of acetone, methyl ethyl ketone, methyl n-propyl ketone, methyl isopropyl ketone, diethyl ketone, methyl n-butyl ketone, ethyl n-propyl ketone, methyl isobutyl ketone, ethyl isopropyl ketone, methyl secondary butyl ketone, cyclopentanone, cyclohexanone, acetophenone, and benzophenone.

4. In a method for preparing compounds of the formula

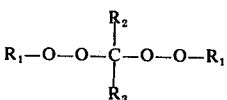

wherein $R_1$, $R_2$, and $R_3$ are independently selected from hydrocarbyl radicals containing from one to sixteen carbon atoms and wherein $R_2$ and $R_3$ can be joined in an alicyclic radical, by the reaction of organic hydroperoxide of the formula $R_1$—O—O—H with a compound of the formula at temperatures in the range of −10°C. to 100°C., the improvement of carrying out the reaction in the presence of a catalyst concentration within the range from about 0.01 to 2 weight per cent of metal based upon the total weight of the starting materials, said catalyst being molybdenum naphthanate.

5. In a method for preparing compounds of the formula

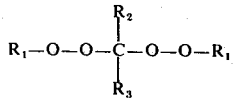

wherein $R_1$, $R_2$, and $R_3$ are independently selected from hydrocarbyl radicals containing from one to sixteen carbon atoms and wherein $R_2$ and $R_3$ can be joined in an alicyclic radical, by the reaction or organic hydroperoxide of the formula $R_1$—O—O—H with a compound of the formula

said organic hydroperoxide being selected from the group consisting of tertiary amyl hydroperoxide, cumene hydroperoxide, cyclohexyl hydroperoxide, cymene hydroperoxide, and tertiary butyl hydroperoxide, and said $R_2$—CO—$R_3$ ketone being selected from the group consisting of acetone, methyl ethyl ketone, methyl n-propyl ketone, methyl isopropyl ketone, diethyl ketone, methyl n-butyl ketone, ethyl n-propyl ketone, methyl isobutyl ketone, ethyl isopropyl ketone, methyl secondary butyl ketone, cyclopentanone, cyclohexanone, acetophenone, and benzophenone, at temperatures in the range of −10°C. to 100°C., the improvement of carrying out the reaction in the presence of a catalyst concentration within the range from about 0.01 to 2 weight per cent of metal based upon the total weight of the starting materials, said catalyst being molybdenum naphthenate.

* * * * *